United States Patent [19]

Papanu

[11] Patent Number: 4,501,847

[45] Date of Patent: Feb. 26, 1985

[54] POLYMERIC ANTITUMOR AGENT

[75] Inventor: Victor D. Papanu, Maryland Heights, Mo.

[73] Assignee: Monsanto Company, St. Louis, Mo.

[21] Appl. No.: 281,544

[22] Filed: Jul. 9, 1981

[51] Int. Cl.³ .................. C08K 3/16; C08F 122/04
[52] U.S. Cl. ................... 524/502; 424/78; 525/327.6
[58] Field of Search .......... 525/328; 424/78

[56] References Cited

U.S. PATENT DOCUMENTS

| | | | |
|---|---|---|---|
| 2,313,565 | 3/1943 | McDowell et al. | 260/78 |
| 3,157,595 | 11/1964 | Johnson et al. | 210/54 |
| 3,308,067 | 3/1967 | Diehl | 252/161 |
| 3,560,529 | 2/1971 | Blumbergs et al. | 549/252 |
| 3,840,499 | 10/1974 | DiGiulio | 260/78.5 T |
| 3,998,907 | 12/1976 | DiGiulio | 260/857 L |
| 4,255,537 | 3/1981 | Fields et al. | 525/328 |

FOREIGN PATENT DOCUMENTS 664326  6/1963  Canada.

OTHER PUBLICATIONS

Hodnett et al., J. Med. Chem., 21(7), 652–657, (1978).
Drougas et al., J. Polymer Sc. 55, 297–302, (1961).

Primary Examiner—John Kight
Assistant Examiner—K. Morgan
Attorney, Agent, or Firm—Scott J. Meyer; James W. Williams, Jr.

[57] ABSTRACT

The disclosure relates to pharmaceutically acceptable amide-imide derivatives of low molecular weight homopolymers of itaconic anhydride having antitumor activity.

6 Claims, No Drawings

POLYMERIC ANTITUMOR AGENT

BACKGROUND OF THE INVENTION

This invention relates to pharmaceutically acceptable amide-imide derivatives of low molecular weight homopolymers of itaconic anhydride having antitumor activity.

Itaconic acid and itaconic anhydride homopolymers and copolymers with other monomeric components are known in the art. Most of these polymeric materials have relatively high molecular weights and are disclosed as useful for various non-pharmaceutical products such as, for example, fibers, plastics and the like products. The preparation of homopolymers of itaconic anhydride having a broadly defined molecular weight range of 350 to 1,500,000 for use as builders in detergent formulations as disclosed in U.S. Pat. Nos. 3,308,067 and 3,560,529 illustrates another such non-pharmaceutical use.

In the pharmaceutical area, Drougas and Guile, *J. Polymer Sci.* 55, 297–302 (1961), describe the biological activity of copolymers of itaconic anhydride and styrene in relation to certain types of cancer. The disclosed molecular weights of these copolymers are in the range of 50,000 to 150,000. Hodnett et al., *J. Med. Chem.* 21 (7), 652–657 (1978), more recently describe the antitumor activity of poly(itaconic acid) against Sarcoma 180. The disclosed molecular weights from viscosity measurements of these polymers range from 44,000 to 250,000 (Table II).

Ammoniated derivatives of some of the foregoing and related types of polymeric materials are disclosed in general terms in various patents, for example, U.S. Pat. Nos. 2,313,565; 3,157,595; 3,840,499; and 3,998,907. Itaconic acid also is mentioned in long lists of monomeric materials in Canadian Pat. No. 664,326 for reaction with sundry olefinic components to provide copolymers which can then be ammoniated to form derivatives having antitumor activity. The disclosed molecular weights of these copolymers broadly range from 500 to 1,500,000.

Low molecular weight copolymers with amide-imide functionality and having antitumor properties are described in U.S. Pat. No. 4,255,537. The disclosed base copolymers are prepared by copolymerization of polycarboxylic anhydrides such as maleic anhydride with olefins such as ethylene and the like monomeric components. The base copolymer molecular weight ranges from about 300 to about 1500.

DESCRIPTION OF THE INVENTION

It has now been found that certain amide-imide derivatives of low molecular weight homopolymers of itaconic anhydride exhibit considerable antitumor activity. The average molecular weight of these homopolymers ranges from about 400 to about 5000. These results are surprising and unexpected since corresponding amide-imide derivatives of certain related homopolymers of acrylic anhydride and 2-methylene glutaric anhydride, respectively, either showed little inhibition of tumor growth (with the former derivative) or were toxic at the only apparent active dose (in the case of the latter derivative).

The base homopolymers of itaconic anhydride can be prepared by catalyzed polymerization of the monomeric material, preferably in the presence of a free-radical promoting catalyst in liquid solvent medium that is a solvent for the monomer and a non-solvent for the polymer formed in the reaction. Conventional peroxide type and azo type free-radical promoting polymerization catalysts are eminently suitable for this purpose, and the benzoyl peroxide exemplified hereinafter is preferred. Other useful catalyst systems soluble in organic solvent media include peroxides such as bis(p-chlorobenzyl)-, acetyl-, and lauroyl peroxides; hydroperoxides such as t-butyl hydroxperoxide and cumene hydroperoxide; and azo compounds such as azobisisobutyronitrile. Inert solvents such as benzene, toluene, halobenzene, haloparaffins and dioxane are useful solvents for the polymerization reaction, and a preferred solvent is 1,2-dichloroethane. The polymerization reaction temperature generally ranges from about 30° C. to about 80° C. and preferably about 70°–75° C., and is carried out for about 3 to about 48 hours.

Following preparation of the base homopolymer, derivatization to the antitumor active amide-imide product is carried out by appropriate ammoniation and heating such that from about 3% to about 35% by weight of the derivatized groups are imide groups. Ammoniation can be carried out by reaction with ammonia gas or aqueous ammonium hydroxide or by reaction with ammonia in organic solvent media. Ammoniation will generally result in formation of geminal half-amide, half-ammonium salt groups. Heating at elevated temperature, e.g. 50°–200° C., for an extended period of time to drive off water from the molecule will result in formation of imide groups. Ammoniation in acetone solvent medium at temperatures of from about 20° C. to about 35° C. followed by ammoniation while refluxing in toluene or xylene until the desired imide percent is obtained is a preferred method of forming the amide-imide derivative. Ammoniation can be conveniently carried out in refluxing toluene at about 110° C. for a period of from about 10 minutes to about 2 hours or in refluxing mixed xylenes at about 135° C. for a period of from about 2 to about 15 minutes.

The ammonium salt group which exists in the amide-imide derivative of the homopolymer can be converted to any other pharmaceutically acceptable cationic salt form such as, for example, sodium and potassium. Thus, conversion to illustrative sodium and potassium salt forms can be readily carried out by ion exchange of the ammonium salt with well known Rohm and Haas IRC-120 resin and similar such conventional ion-exchange resins in the sodium and potassium ion forms, respectively.

For purposes of illustration and not limitation, the preferred homopolymers of itaconic anhydride as appropriately derivatized can be represented as having the following structural units or groups:

(a) half-amide, half-ammonium salt

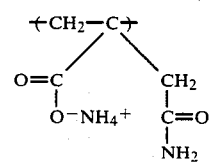

and (b) imide

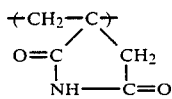

The respective (a) and (b) units or groups are distributed along a substantially linear continuous carbon atom molecule. From about 3% to about 35% by weight of these units should be (b) imide with the balance being principally (a) half-amide, half-carboxylate salt units (preferably ammonium salt as illustrated). These units can be positioned randomly within the chain and/or randomly within the polymer. Various end groups also can be introduced into the polymer by virtue of the organic moieties present in the free-radical initiator or by means of chain transfer from the solvent. For example, use of benzoyl peroxide initiator can result in the presence of phenyl end groups on some of the polymer chains.

The molecular weight of the underivatized homopolymers of itaconic anhydride used in the present invention can be estimated in terms of the number average molecular weight ($\overline{M}_n$), weight average molecular weight ($\overline{M}_w$), or in terms of intrinsic viscosity. The number average molecular weight ($\overline{M}_n$) of these polymeric materials as determined by Vapor Pressure Osmometry in dimethylformamide (DMF) at 90° C. preferably ranges from about 400 to about 5000. Specific viscosity ($\eta_{sp}$) of a 0.5% solution (wt. vol.) in acetone at 25° C. preferably ranges from about 0.01 to about 0.03 dl/g. The $\overline{M}_n$ and $\overline{M}_w$ were also determined by a Gel Permeation Chromatographic (GPC) technique. A preferred example has $\overline{M}_n$ 1400, $\overline{M}_w$ 2300 as determined by GPC and $\eta_{sp}$ 0.014 (0.5% in acetone at 25° C.)

The derivatized homopolymer product as prepared above can be placed into any suitable dosage form for the desired end use and administered to a warm-blooded animal by a variety of parenteral routes, especially intravenously and intraperitoneally. Such administration preferably is in aqueous solution such as in sterile water, physiologically normal saline (0.9% NaCl) and the like sterile injectable forms and can be carried out by suitable reconstitution of solid product. The derivatized homopolymer product also can be administered orally in the form of tablets, powders, capsules, elixers and the like dosage forms. The active product can be used in admixture with common solid and liquid fillers, diluents, carriers, suspending agents and adjuvants such as, for example, cornstarch, lactose, talc, stearic acid, magnesium stearate, carboxymethyl cellulose, gelatin, acacia and locust bean gums, alcohol, water, dimethylsulfoxide, vegetable oils and the like pharmaceutically acceptable materials. The liquid oral dosage form also preferably is solid reconstituted in liquid mixture at the time of administration in order to maintain stability of the dual groupings of amide and imide.

Dosages can vary widely as will be apparent from the more detailed illustrative examples set forth hereinbelow. Thus, in tests for activity against Lewis lung carcinoma implanted subcutaneously in B6D2F$_1$ mice, substantial inhibition of primary tumor growth was observed in animals treated with the homopolymers made in accordance with this invention when administered over a wide range of dosage. The Lewis lung carcinoma is generally recognized as a severely intractable tumor condition against which most antitumor compounds are ineffective.

The following detailed examples will further illustrate the invention although it will be appreciated that the invention is not limited to these specific examples.

EXAMPLE 1

Itaconic Anhydride Recrystallization 60 g (0.54 mole) of crude itaconic anhydride (Eastman Org. Chem.) and 120 ml of toluene were placed in a 250 ml Erlenmeyer flask equipped with a magnetic stirrer. The contents were heated to 75° C. for 5 minutes and filtered (while still hot) through a coarse grade sintered glass Buchner filter. The solution was stored at 5° C. for 16 hours. Toluene was removed by decantation and crystals were dried under pump vacuum (<0.5 mm Hg) for 18 hours at ambient temperature. 50 g (83%) was obtained, mp. 68.5°–70.0° C. (literature mp. 67°–68° C.). $^1$H NMR (60 MHz), CDCl$_3$, δ: 6.62 (1H, triplet J=2.5 Hz) 5.91 (1H, triplet J=2.5 Hz); 3.61 (2H, triplet J=2.5 Hz). IR, (1% KBr), $\nu$cm$^{-1}$: 3120, (C=C—H); 1840, 1760 (C=O); 1660 (C=C).

Itaconic Anhydride Polymerization

A portion of the above recrystallized itaconic anhydride, 22.4 g (0.2 mole) was added to 300 ml of 1,2 dichloroethane in a 500 ml three necked round bottomed flask (previously flamed and cooled under N$_2$) equipped with a magnetic stirrer and thermometer. The mixture was heated to 55°–60° C. When solution occurred, 2.4 g (0.01 mole) benzoyl peroxide was added. The temperature was raised to 70° C. and maintained for 30 hr. The polymer precipitated during this time. Heating was stopped and the slurry was stirred for 16 hr at ambient temperature. The solid was removed via filtration and slurried in 250 ml of 99 mole % 1,4-dioxane for 3 hr at ambient temperature. The polymer was filtered and dried under pump vacuum for 4 hr. The product yield was 11.6 g (52%). It contained 3–5% unreacted monomer as shown by $^1$H NMR analysis. Sp. visc. (0.5 wt. % in acetone)=0.014; M$_n$=1400, M$_w$=2300.

Amide-Imide Derivatization

A portion of the above-prepared solid itaconic anhydride polymer, 10 g, was dissolved in 110 ml of reagent grade acetone. This solution was simultaneously added via syringe pump at a rate of 11 ml/min. along with anhydrous NH$_3$ to 150 ml of reagent grade acetone in a 500 ml four necked round bottom flask. It was equipped with a mechanical stirrer, thermocouple, condenser with a solution inlet tube down the inside, and a NH$_3$ gas dispersion tube. The addition of NH$_3$ was continued 2½ hr after the addition of the solution was completed. An exotherm of 10°–15° C. occurred initially but subsided after 1 hr. The slurry color changed from yellow to nearly white during this procedure. The solid was removed via filtration and dried under pump vacuum for 16 hr.

The dried solid was added to 70 ml of toluene in a three necked 100 ml round bottom flask equipped with a NH$_3$ dispersion tube, mechanical stirrer, and reflux condenser with an outlet tube attached. The slurry was heated to reflux and maintained for 80 min. while NH$_3$ was bubbled through it. 13% imide was shown to be present in the solid product by IR analysis. The slurry was then reheated and maintained at reflux for another 40 min. The IR analysis then showed 20% imide to be present. The product became orange colored during imidation. Much color was removed by triturating the solid for 96 hr in 300 ml of $CH_3CN$ with 5–10 ml $H_2O$ added, followed by 24 hr in 200 ml acetone with 2–5 ml $H_2O$ present. The solid was filtered and dried under water aspirator vacuum for 2 hr. It was then dissolved in 100 ml deionized water, filtered through a $20\mu$ Millipore filter, and freeze dried for 24 hr. The yield was 9.0 g. Elemental analysis: found, C, 41.0%; H, 7.2%; N, 11.7%. IR; imide C=O @ 1710 $cm^{-1}$, amide C=O @ 1670 $cm^{-1}$, ammonium carboxylate C=O @ 1570 $cm^{-1}$. $^1H$ NMR (90 MHz), $D_2O$, $\delta$: broad hump 1.5–3.0, singlet 7.1 (aromatic endgroup).

EXAMPLE 2

Another portion of the above recrystallized itaconic anhydride was polymerized and derivatized as follows:

Itaconic anhydride, 22.4 grams (0.2 mole), and 300 milliliters of 99 mole % pure 1,4-dioxane were placed in a three-necked, 500 milliliter round-bottomed flask equipped with a magnetic stirrer and thermometer. Benzoyl peroxide, 2.4 grams (0.01 mole), was added at a solution temperature of 30° C. The solution was stirred for 30 hours at 70° C., during which time a precipitate formed. The suspension was cooled to 40° C. and filtered. The precipitate was washed with 500 milliliters of methylene chloride, and dried under pump vacuum (<1 torr) at ambient temperature for 16 hours. No unreacted monomer could be detected by $^1H$ NMR spectroscopic analysis.

The dried solid was dissolved in 200 milliliters of reagent grade acetone and introduced at a rate of 8 milliliters/minute concurrently with addition of anhydrous ammonia into a 500 milliliter four-necked, round-bottom flask containing 150 milliliters of reagent grade acetone. The flask was equipped with a mechanical stirrer, thermocouple, condenser and anhydrous ammonia inlet dispersion tube. Addition of the ammonia was continued for 2 hours after the initial acetone solution had been added. The precipitate which formed was filtered and stirred in 200 milliliters of acetonitrile for 6 hours to remove the color. The resulting sample was filtered and stirred in 200 milliliters of acetone for 24 hours. The product was nearly colorless and was filtered and dried under pump vacuum for 6 hours. The dried sample was dissolved to a 10% solution in deionized water. The pH was adjusted to 9.5 with concentrated ammonia water and the solution was filtered through a 20 micron Millipore filter and freeze-dried for 50 hours. A yield of 17 grams of product was obtained. Approximately 3% imide was present as determined by infrared spectroscopic analysis.

EXAMPLE 3

Samples of the final products prepared in Examples 1 and 2, above, were dissolved in distilled water and the pH adjusted to 9.5 with concentrated $NH_4OH$. The solutions were filtered through a $0.2\mu$ filter and freeze dried prior to submission for pharmaceutical evaluation. In this evaluation, the samples were tested at various dosages for their antitumor activity against Lewis lung carcinoma. In this test, $10^6$ Lewis lung cells were implanted s.c. in the right flank of female $B6D2F_1$ mice (10 per group). The test samples were dissolved in sterile 0.9% NaCl solution and administered i.p. in a volume of 0.5 ml per mouse. Tumors were measured in perpendicular diameters one day 14 and tumor volume was calculated by the formula: length$\times$width$^2\times 0.5$. Mean and median tumor volumes were calculated for each treatment group (T) and were compared with untreated controls (C) to obtain a T/C ratio. The following tables set forth the results for the two samples prepared from the final products of Examples 1 and 2.

TABLE 1

EVALUATION OF EXAMPLE 1 PRODUCT IN sc LEWIS LUNG CARCINOMA

| Compound Imide % | Dose (mg/kg. ip qD 1-5) | Wt. Change (gm) Day 7 | Wt. Change (gm) Day 14 | Tumor Growth Inhibition (Day 14) N.P.[a] | Median Volume ($mm^3$) | T/C[b] | Mean Volume ($mm^3$) ± S.D. | T/C[b] |
|---|---|---|---|---|---|---|---|---|
| 20% | 2000 | Toxic | | | | 10/10 dead by Day 6 | | |
| | 800 | +0.4 | +1.5 | 4/10 | 299 | .19 | 294 ± 293[t] | .18 |
| | 320 | +0.9 | +1.3 | 1/10 | 550 | .35 | 696 ± 531[t] | .39 |
| | 128 | +1.4 | +1.3 | 0/10 | 1617 | 1.02 | 1425 + 510 | .85 |
| | 51.2 | +1.1 | +1.2 | 0/10 | 1703 | 1.07 | 1807 ± 603 | 1.08 |
| | 20.5 | +0.9 | +1.2 | 0/10 | 1584 | 1.00 | 1605 ± 414 | .96 |
| | 8.19 | +2.0 | +1.1 | 0/10 | 1372 | .86 | 1591 ± 619 | .95 |
| Untreated Controls | | +1.6 | +1.5 | 0/10 | 1993 | | 1960 ± 498 | |
| | | +1.5 | +0.9 | 0/10 | 1628 | 1587 | 1638 ± 653 | 1676 ± 608 |
| | | +1.6 | +1.1 | 0/10 | 1362 | | 1555 ± 821 | |
| | | +3.1 | +0.7 | 0/10 | 1538 | | 1551 ± 357 | |

[a]N.P. = mice without palpable tumors on day 14/total
[b]T/C = ratio of tumor volume in treated group relative to untreated controls
t = Significantly different from untreated control at p .01 by Student's t test
qD = daily dosage, days 1 to 5

TABLE 2

EVALUATION OF EXAMPLE 2 PRODUCT IN sc LEWIS LUNG CARCINOMA

| Compound Imide % | Dose (mg/kg. ip qD 1-5) | Wt. Change (gm) Day 7 | Wt. Change (gm) Day 14 | Tumor Growth Inhibition (Day 14) N.P.[a] | Median Volume ($mm^3$) | t./C[b] | Mean Volume ($mm^3$) + S.D. | T/C[b] |
|---|---|---|---|---|---|---|---|---|
| 3% | 2000 | Toxic | | | | 10/10 dead by day 2 | | |
| | 800 | +0.2 | +1.6 | 0/8 | 117 | .07 | 272 = 264[t] | .16 |
| | 320 | +1.3 | +1.1 | 1/10 | 625 | .39 | 505 = 351[t] | .30 |
| | 128 | +1.6 | +1.1 | 0/10 | 973 | .61 | 885 = 411[t] | .53 |
| | 51.2 | +1.1 | +1.8 | 0/10 | 1116 | .70 | 1268 = 440 | .76 |

TABLE 2-continued
EVALUATION OF EXAMPLE 2 PRODUCT IN sc LEWIS LUNG CARCINOMA

| Compound Imide % | Dose (mg/kg. ip qD 1-5) | Wt. Change (gm) Day 7 | Day 14 | N.P.[a] | Median Volume (mm³) | t./C[b] | Mean Volume (mm³) + S.D. | | T/C[b] |
|---|---|---|---|---|---|---|---|---|---|
| | 20.5 | +1.0 | +0.7 | 0/10 | 1447 | .91 | 1554 = 471 | | .93 |
| | 8.19 | +1.2 | +1.8 | 0/10 | 1432 | .90 | 1638 = 685 | | .98 |
| Untreated | | +1.6 | +1.5 | 0/10 | 1993 | | 1960 = 498 | | |
| Controls | | +1.5 | +0.9 | 0/10 | 1628 | 1587 | 1638 = 653 | 1676 + 608 | |
| | | +1.6 | +1.1 | 0/10 | 1362 | | 1555 = 821 | | |
| | | +3.1 | +0.7 | 0/10 | 1538 | | 1551 = 357 | | |

[a] N.P. = mice without palpable tumors on day 14/total
[b] T/C = ratio of tumor volume in treated group relative to untreated controls
t = Significantly different from untreated control at p <.01 by Student's t test
qD = daily dosage, days 1 to 5

In the above examples, Imide % was determined by IR spectrometry substantially as described in U.S. Pat. No. 4,255,537.

Various other examples will be apparent to the person skilled in the art after reading the instant disclosure without departing from the spirit and scope of the invention and it is intended that all such examples be included within the scope of the appended claims.

What is claimed is:

1. An antitumor-active composition of matter selected from the group consisting of low molecular weight homopolymers of itaconic anhydride having average molecular weights of from about 400 to about 5000 and derivatized to contain (a) half-amide, half-carboxyl acid groups and (b) imide groups in which said imide groups comprise from about 3% by weight to about 35% by weight of said derivatized groups, and the pharmaceutically acceptable cationic salt derivatives of said derivatized homopolymers.

2. The composition of matter of claim 1 in which the derivatized groups are (a) half-amide, half-ammonium salt and (b) imide groups.

3. A pharmaceutical composition having antitumor activity which comprises, as active ingredient, the composition of matter of claim 1, in association with a significant amount of a pharmaceutically acceptable carrier.

4. A pharmaceutical composition for parenteral administration and useful for the treatment of Lewis lung carcinoma which comprises, as active ingredient, the composition of matter of claim 1, in association with a significant amount of a sterile injectable pharmaceutically acceptable carrier.

5. Method for the treatment of Lewis lung carcinoma in a warm blooded animal which comprises administering to said animal an effective amount for inhibitory growth of said carcinoma of the composition of matter of claim 1.

6. Method for the treatment of Lewis lung carcinoma in a warm blooded animal which comprises administering parenterally to said animal an effective amount for inhibitory growth of said carcinoma of the composition of matter of claim 1.

* * * * *